United States Patent [19]

Cohen et al.

[11] Patent Number: 5,114,721
[45] Date of Patent: May 19, 1992

[54] PREPARATION OF T-CELL AND T-CELL MEMBRANE FOR USE IN PREVENTION AND TREATMENT OF AUTOIMMUNE DISEASES

[75] Inventors: Irun R. Cohen; Meir Shinitzky, both of Rehovot, Israel; Richard L. Edelson, Westport, Conn.

[73] Assignee: Yeda Research and Development Co. Ltd., Rehovot, Israel

[21] Appl. No.: 323,705

[22] Filed: Mar. 15, 1989

Related U.S. Application Data

[63] Continuation-in-part of Ser. No. 910,876, Sep. 23, 1986, Pat. No. 4,996,194, which is a continuation-in-part of Ser. No. 648,802, Sep. 7, 1984, Pat. No. 4,634,590.

[30] Foreign Application Priority Data

Mar. 15, 1988 [IL] Israel .......................... 85746

[51] Int. Cl.$^5$ .................... A61K 31/35; A61K 35/14
[52] U.S. Cl. ................... 424/534; 514/455; 514/825; 514/866; 514/885; 514/903
[58] Field of Search ............. 424/88, 534; 514/885, 514/825, 866, 903, 455

[56] References Cited

U.S. PATENT DOCUMENTS

| | | | |
|---|---|---|---|
| 4,612,007 | 9/1986 | Edelson | 604/5 |
| 4,634,590 | 1/1987 | Cohen et al. | 424/88 |
| 4,684,521 | 8/1987 | Edelson | 424/101 |
| 5,036,102 | 7/1991 | Bachynsky et al. | 514/455 |

OTHER PUBLICATIONS

Lischka et al., CA 89:100269a.
Roberts et al., CA 91:69662p.
Yurkow et al., J. Bio. Chem., 262(18), pp. 8439–8442 (1987).
Bohnert et al., CA 88:3899c.
Edelson et al., N. Engl. J. Med., 316, pp. 297–303 (1987).
Laskin et al., Proc. Natl. Acad. Sci. USA, 82, pp. 6158–6162 (1985).
Lider et al., Proc. Natl. Acad. Sci. USA, 84, pp. 4577–4580 (1987).
Ben-Nun et al., J. Immunol., 129(1) pp. 303–308 (1982).

*Primary Examiner*—Frederick E. Waddell
*Assistant Examiner*—Kimberly R. Jordan
*Attorney, Agent, or Firm*—Browdy and Neimark

[57] ABSTRACT

Pharmaceutical preparations are provided for preventing or treating autoimmune diseases in which the active principle is activated T-lymphocyte cells, specific for the autoimmune disease to be treated, which cells have been treated by incubation with a photoactivatable psoralen cross-linking agent, such as 8-methoxypsoralen, and then photoactivated. The active principle may also be the membrane fraction of such cells. Such preparations may be formulated into pharmaceutical compositions and administered to prevent or treat autoimmune disesases.

16 Claims, 1 Drawing Sheet

PREPARATION OF T-CELL AND T-CELL MEMBRANE FOR USE IN PREVENTION AND TREATMENT OF AUTOIMMUNE DISEASES

CROSS-REFERENCE TO RELATED APPLICATIONS

The present application is a continuation-in-part of Ser. No. 910,876, filed Sep. 23, 1986, now U.S. Pat. No. 4,996,194 which, in turn, was a continuation-in-part of Ser. No. 648,802, filed Sep. 7, 1984, now U.S. Pat. No. 4,634,590, the entire contents of each of which applications are hereby incorporated by reference.

FIELD OF THE INVENTION

The present invention relates to novel pharmaceutical compositions for prevention or treatment of autoimmune diseases, which contain as an active ingredient an effective quantity of activated T-cells which are specific to the autoimmune disease being treated, which T-cells have been subjected to a photo-activated psoralen treatment, or the membrane fraction of such treated T-cells.

BACKGROUND OF THE INVENTION

The etiological agents of autoimmune disease are endogenous lymphocytes which attack normal constituents of the individual. Autoimmune diseases share this common feature of being caused by the immune system's attacking the individual's own tissues. At the seat of all autoimmune diseases are the autoimmune lymphocytes which specifically recognize the individual's particular target antigens. Among the autoimmune diseases that are commonly recognized as such are rheumatoid arthritis, multiple sclerosis, some forms of diabetes mellitus, thyroiditis, myasthenia gravis, and anterior uveitis.

It has been found possible to grow, as long term cell lines, T-lymphocytes responsible for causing autoimmune diseases in laboratory animals. Among these diseases are encephalomyelitis, arthritis, and thyroiditis. Under certain conditions, these cells were found to be effective agents for vaccination against such specific autoimmune diseases. The lymphocytes were attenuated prior to injection so that they would not cause the autoimmune diseases. It was found that these vaccinations were quite effective in rendering the animals immune, or less sensitive (i.e., the disease was less severe) to such disease. Furthermore, when such animals which already showed symptoms of the disease were inoculated with these cells, the diseases were quite effectively treated.

As described by Cohen and Shinitsky, *Proc. Natl. Acad. Sci. USA*. 84:4577, 1987, and in parent application Ser. No. 910,876, T-cell vaccines against autoimmune diseases can be prepared by treating these T-cells with chemical cross-linkers, such as glutaraldehyde and formaldehyde. The membranes of these cells, treated with the cross-linking agents, were also effective as active ingredients of the vaccines. These compositions can also be used for alleviation of symptoms of these autoimmune diseases.

As a group, the psoralens, of which 8-MOP is a member, are compounds which have been found to cross-link molecules such as proteins very selectively under the influence of ultraviolet light, generally 320–400 nm in wavelength. These compounds, also known as furocoumarins, occur naturally in more than two dozen plant species. Two of the psoralen analogs, 8-methoxypsoralen and 4,5′,8-trimethylpsoralen, are used clinically in the photochemotherapy of skin diseases such as psoriasis, mycosis fungoides, vitiligo, and eczema. Typically, patients are administered the psoralen orally or topically, and are then exposed to a measured dose of ultraviolet irradiation.

Recently, 8-methoxypsoralen, or 8-MOP, has been used to damage tumor cells circulating in the blood, Edelson et al., *N. Eng. J. Med.*, 216:297, 1987. The blood cells were irradiated with UVA in an extracorporeal apparatus. The treated blood cells were returned to the body, leading to a response of the immune system against the tumor cells. The mechanism of the tumor cell damage was considered to be due to cross-linking of DNA by means of 8-MOP.

It has previously been assumed that the biological effects of psoralens are associated with their ability to bind covalently and cross-link DNA. However, Yurkow et al., *J. Biol. Chem.*, 262 (18):8439–8442, 1987, disclose that a psoralen receptor was found in cytoplasmic and plasma membrane fractions of HeLa cells following sodium dodecyl sulfate-polyacrylamide gel electrophoresis. This cellular protein exhibits specific affinity for the psoralen compounds and becomes photoalkylated by these compounds. Yurkow et al further disclose that psoralen receptors in HeLa cells are a protein having a molecular mass of approximately 22,000 daltons. Binding of photoactivated psoralen to its receptor actually alters the proliferation and differentiation states of different cell types. Thus, the psoralens do not serve as general chemical cross-linkers but as very specific receptor activating ligands which activate the receptor only after photoactivation.

Additional evidence of psoralens not necessarily interacting directly with DNA is reported by Laskin et al., *Proc. Nat. Acad. Sci. USA*, 82: 6158–6162, 1985. Specific, saturable, high-affinity binding sites for 8-MOP have been identified on HeLa cells, and specific binding on other cell lines has also been found for 8-MOP.

SUMMARY OF THE INVENTION

It is an object of the present invention to provide T-cells cross-linked with a photoactivated psoralen cross-linker or membranes of such T-cells.

It is another object of the present invention to provide compositions which can be used for the prevention or treatment of autoimmune disease.

It is still a further object of the present invention to provide T-cells cross-linked at the specific receptor for psoralen molecules.

It is yet another object of the present invention to provide a method for the prevention or treatment of autoimmune diseases by administering such preparations.

According to the present invention, T-cells are cross-linked with a photoactivatable psoralen cross-linker. The cross-linked T-cells may be used in intact form or membrane fractions of the lysed cross-linked T-cells may be used. A particularly useful photoactivatable cross-linker for this purpose is 8-methoxypsoralen, hereinafter designated 8-MOP.

The cross-linking is effected by treating the cells with the cross-linking agent and then subjecting the so treated cells to light of an appropriate wavelength to effect the cross-linking. Vaccines are then prepared from the cross-linked cells or membranes separated therefrom. Alternatively, pharmaceutical compositions can be prepared which are useful in alleviating the symptoms of autoimmune diseases.

The cross-linking agents for use in the present invention are photoactivatable psoralen cross-linking reagents which have been found to be very specific for certain receptors on the cells, and which only cross-link at those receptors. These receptors are the 22,000 dalton protein found in cell membranes as reported by Yurkow et al, supra. This is in contrast to conventional cross-linkers such as glutaraldehyde, which cross-link indiscriminately. Among the psoralens which can be used in the present invention are any photoactivatable psoralen derivatives that cross-link selectively. Among these compounds may be mentioned psoralen, 8-methoxypsoralen, 4, 5',8-trimethylpsoralen, 4',5'-dihydropsoralen, 3-carbethoxypsoralen, 4',5'-dihydro 3-carbethoxypsoralen, 5-methoxypsoralen, 4'-(hydroxymethyl)-4,5',8-trimethylpsoralen, aminomethyltrioxypsoralen, and the like.

The T-cells or membranes thereof which are cross-linked by these photoactivatable cross-linking agents were found to be useful as vaccines for autoimmune diseases, as well as for treatment of such diseases.

DETAILED DESCRIPTION OF THE INVENTION

Figure 1:
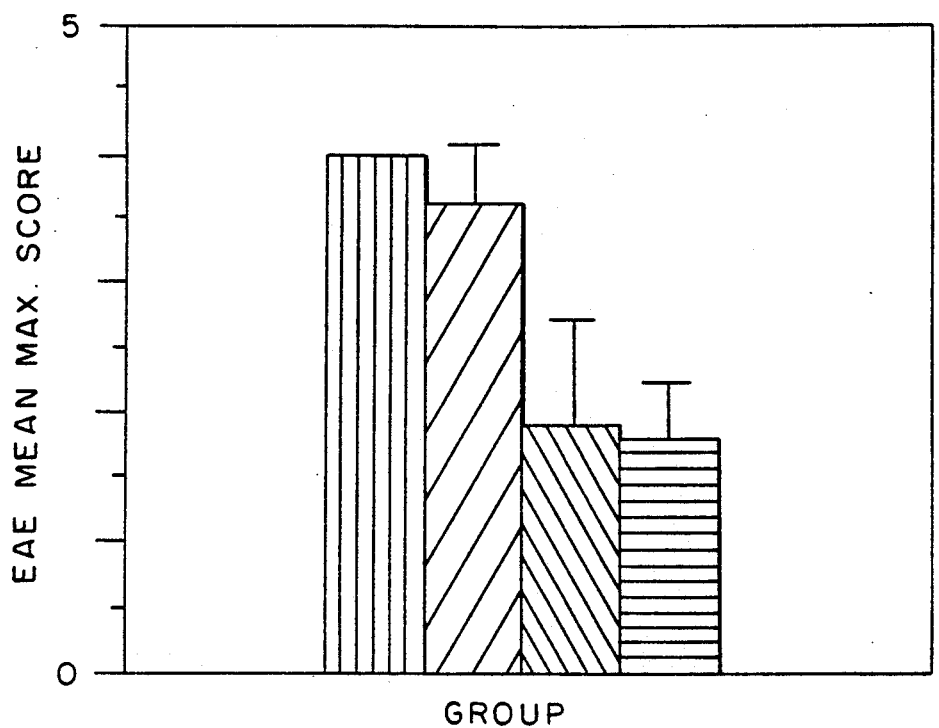
FIG. 1 illustrates the vaccination against EAE using 8-MOP-UVA treated cells or T-cell membranes.

According to the present invention, there are provided pharmaceutical preparations which contain as their active ingredient specific activated autoimmune T-lymphocytes which have been cross-linked by means of a photoactivatable psoralen cross-linking agent, or membrane material separated from such specific cross-linked T-lymphocytes.

The T-lymphocyte cells which may be used for the purpose of the present invention include any activated T-cell which is specific for an autoimmune disease. The T-lymphocyte cells of the present invention may be derived from an established cell line or may be taken from the circulatory or lymphatic systems of a subject, e.g., a mouse, a rat or a human. Additionally, the T-lymphocyte cells may be taken directly from a patient who is to be treated for a specific autoimmune disease. The cells must also be "activated". Within the present application, "activated T-lymphocyte cell" means a T-lymphocyte cell which has been exposed to a specific antigen or a mitogen capable of inducing an immune response by the T-lymphocyte cell. Suitable mitogens are known in the art and include concanavalin A, phytohemagglutinin, and poke-weed mitogen. As the T-cells must be both specific for an auto-immune disease and activated, the non-specific activating agents, such as mitogens, should only be used on cells which are already specific for an autoimmune disease, such as established cell lines which are specific for an autoimmune disease, or cells taken from the circulatory or lymphatic systems of a subject which already has the disease. The T-cells removed from such a subject will include T-cells specific for that disease. When non-specific T-cells are to be activated, a specific antigen should be used as the activating agent in order both to make the T-cells specific to that antigen and to activate them.

As it is the cell membrane receptors which are the operative portion of the T-cells in accordance with the present invention, the specific biological activity of the T-cells used is not important. Thus, any of the known T-cell subsets may be used.

The T-cells may optionally be pressure treated in accordance with the procedure described in parent application Ser. No. 910,876. Such a procedure comprises subjecting the cells to hydrostatic pressure and releasing such pressure in a gradual manner. The amount of pressure and time at that pressure are selected such that substantially no shedding of membrane proteins occurs. Typical conditions for such pressure activation of cells are a build up of pressure during about 5 minutes, going up from about 500 to about 1000 atm, maintaining the pressure for about 5 minutes and gradually releasing the pressure during about 5 minutes. Such treatment causes a vertical displacement of the membrane constituents such that they effectively "pop up" and the antigenicity of the cells becomes augmented. The photoactivated cross-linking treatment in accordance with the present invention may be before or after such pressure treatment.

If the photoactivated cross-linking treatment is prior to pressure treatment, then the pressure treatment may be conducted under conditions which result in an effective shedding of membrane material which will retain a high degree of antigenic activity. Typical conditions for the shedding of the active material are pressures of the order of 500 to about 1500 atm, the build up of pressure being gradually over about 5 minutes, maintaining such pressure at the upper level for about 10 to 45 minutes, and gradually releasing the pressure over 5 to 15 minutes. The membrane components shed during such pressure treatment, including both the membrane fragments and large protein aggregates and the soluble membrane proteins, may be used in accordance with the present invention.

The cells being treated in accordance with the present invention may also optionally be treated with a standard chemical cross-linking agent such as formaldehyde or glutaraldehyde. Such may be either before or after receiving the photoactivated cross-linking treatment and either before or after or in lieu of pressure treatment. Preferably, the chemical cross-linking treatment is after photoactivated cross-linking treatment so as not to interfere with the specific receptor site at which the selective photoactivated cross-linking occurs. Similarly, the cells may also optionally be treated with a disrupting agent which causes the cell's cytoskeleton to dissociate. Such disrupting agents include the chemicals cytochalasin and colchicine, although other disrupting agents are known in the art and may also be used. The disrupting agent treatment may also be prior to, after, or without pressure treatment (although it should be before pressure treatment intended to obtain shedding of membrane components), prior to, after or without chemical cross-linking agent treatment, and prior to or after photoactivated cross-linking agent treatment. If membrane fragments of lysed cells are to be used, all of the above treatments should occur prior to lysing. Specific disclosure of conditions, etc., for pressure-treatment, chemical cross-linking agent treatment and disrupting agent treatment is set forth in parent application Ser. No. 910,876, which is incorporated herein by reference.

The T-cells, preferably in an amount of about $5-10 \times 10^6$/ml, suspended in tissue culture medium, are cross-linked by incubating with a mild photoactivatable psoralen cross-linking agent, about 50 to about 500 ng/ml, and subjecting the treated material to light of a suitable wavelength for a period of from about 5 to about 60 minutes. In the case of 8-MOP, the light used is UVA radiation, preferably at a wavelength of 350 nM and at a dose of 1-2 Joules. The cross-linked materials are effective vaccine materials even after lysing of the cells.

Cross-linked membranes are obtained by lysing the cross-linked T-cells, such as by homogenization of the cells in phosphate buffered saline diluted in distilled $H_2O$, removing the nuclei and cell debris by centrifugation, and subjecting the supernatant containing the membranes to ultracentrifugation and retaining the pellet which comprises the cross-linked membranes. The membranes obtained from treated T-cells were effective in vaccinating rats against either EAE or adjuvant arthritis.

Although 8-MOP-UVA was originally postulated to affect cells by the cross-linking of DNA, the present results indicate that it can exert an effect on the T-cell membrane, thus confirming the reports of Yurkow et al and Laskin et al, supra. It is apparently the specific cross-linking of the 22 KD psoralen receptor on the cell surfaces which causes the greatly improved results over non-psoralen treated cells. Thus, any photoactivatable psoralen compound which is recognized by the same receptor as recognizes 8-MOP can be used in accordance with the present invention. These include psoralen, 8-methoxypsoralen, 4, 5',8-trimethylpsoralen, 4',5'-dihydropsoralen, 3-carbethoxypsoralen, 4',5'-dihydro 3-carbethoxypsoralen, 5-methoxypsoralen, 4'-(hydroxymethyl)-4,5',8-trimethylpsoralen, aminomethyltrioxypsoralen, and the like.

As it is this selective cross-linking which causes the outstanding results of the present invention, the use of these particular cross-linking agents would not have been obvious to one of ordinary skill in the art aware of the disclosure of parent application Ser. No. 910,876. Photoactivated psoralens are not merely another species of cross-linkers. They only cross-link specific receptors and, as such, cause activation of certain biological functions of the cells. It is this specific receptor activation activity of the psoralens which greatly improves the utility of the cells for the prevention and treatment of auto-immune diseases. This is a completely different function as compared to the general chemical cross-linkers, such as formaldehyde and glutaraldehyde, of the parent application. Those skilled in this art realize that the less the amount of cross-linking of the cell surface, the safer will be the treated cells as a pharmaceutical. Thus, the specifically cross-linked cells and membranes of the present invention are superior to and unobvious from the generally cross-linked cells and membranes of the parent application, even if the results are substantially equivalent.

A number of experiments were conducted to test whether membranes of 8-MOP-UVA-treated T-cells could be used as vaccines which would be effective against autoimmune diseases and which can also be used for treatment of such diseases.

EXAMPLE 1

FIG. 1 illustrates the vaccination against EAE using 8-MOP-UVA treated T-cells or T-cell membranes. Groups of five Lewis rats were inoculated intraperitoneally with $20 \times 10^6$ cells of the Z1a anti-myelin basic protein cell line. The T-cells were activated before inoculation, as described in Ben-Nun et al., *J. Immunol.*, 129:303, 1982. The activated T-cells ($80 \times 10^6$ in 10 ml medium) were then treated either with gamma-irradiation (1500 Rads) as described in Ben-Nun et al., ibid., or with 8-MOP. The 8-MOP treated cells were incubated with 500 ng/ml of 8-MOP by placing 6 ml increments of the cells in a 9 cm plastic tissue culture plate and rotating with the 8-MOP at room temperature for 30 minutes in the dark. The 8-MOP T-cells were then irradiated with UVA, 350 nM at a dose of 2 joules.

Membranes were prepared from the 8-MOP-UVA treated T-cells in the following manner: The cells in phosphate buffered saline were diluted 1:3 in distilled water and were homogenized in a Polytron apparatus (setting no. 7 for two minutes). Nuclei and cell debris were removed by centrifugation for 10 minutes at 2000 rpm. The supernatant fraction containing the membranes was centrifuged at $90,000 \times g$ for 90 minutes, and the pellet was suspended in 1 ml of phosphate buffered saline. Each rat was inoculated intraperitoneally with the sedimented membrane fraction, obtained from an equivalent of $60 \times 10^6$ T-cells.

Three treatments with cells or membranes were administered to the rats at weekly intervals. One week after the last treatment, the rats were challenged by immunization with 50 μg of myelin basic protein in complete Freunds' adjuvant to induce EAE as described by Ben-Nun, ibid. Clinical paralysis and mortality were recorded.

In FIG. 1, the groups of rats are: striped column, unvaccinated rats; column with diagonal stripes, rats vaccinated with irradiated Z1a cells; dotted column, rats vaccinated with 8-MOP Z1a cells; black column, rats vaccinated with 8-MOP Z1a membranes.

It can readily be seen that the gamma-irradiated Z1a cells failed to induce resistance to EAE (the clinical score was 3.6 with 40% mortality). In contrast, the 8-MOP-UVA treated whole Z1a cells, or the membranes of these cells, induced resistance to EAE expressed as a significant reduction in EAE score (1.9 and 1.8 with no mortality).

EXAMPLE 2

To confirm the general effectiveness of membranes from T-cells treated with 8-MOP-UVA, rats were vaccinated with 8-MOP-UVA treated membranes of the A2b cell clone. This clone was found to vaccinate rats against adjuvant arthritis if the A2b cells were cross-linked by glutaraldehyde or formaldehyde.

Groups of 10 Lewis rats were or were not treated with membranes obtained as described in example 1. Each inoculum contained membranes obtained from $10^8$ activated A2b T-cells. After three intraperitoneal inoculations, the rats were challenged with *M. Tuberculosis* (H37Ra) as described by Lider et al., op. cit., to induce adjuvant arthritis. The degree of clinical arthritis was observed and scored.

Figure 2:
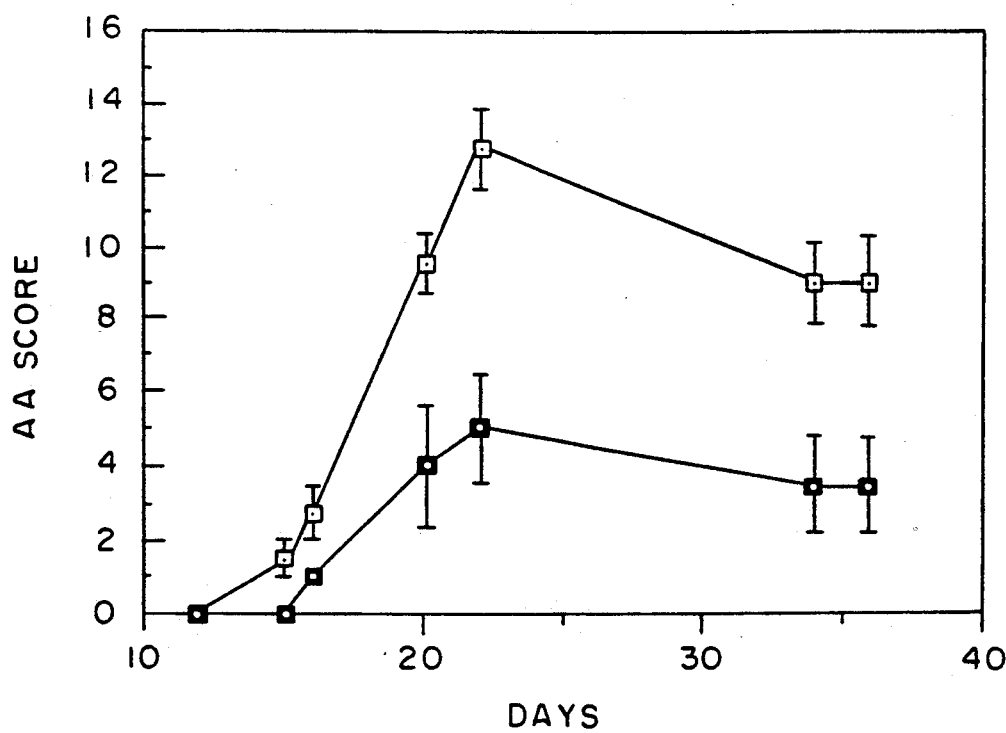
FIG. 2 shows the results of 8-MOP-UVA treated T-cells.

FIG. 2 illustrates the results of vaccination against adjuvant arthritis using membranes of 8-MOP-UVA treated T-cells. In FIG. 2, the white squares with a central dot are the controls; the black squares with white central dot are the groups vaccinated with A2bMB (8-MOP).

It can be seen that vaccination with membranes of A2b cells treated with 8-MOP-UVA significantly reduced the severity of arthritis. The compositions of the present invention were also tested with regard to their efficacy for alleviating the symptoms of autoimmune disease, with encouraging results.

EXAMPLE 3

Table 1 illustrates the effectiveness of 8-MOP-UVA treated T-cells in vaccinating against autoimmune diabetes. Non-obese diabetic (NOD) mice spontaneously develop autoimmune insulin-dependent diabetes mellitus (IDDM) similar to the IDDM appearing in human patients. Autoimmune attack against pancreatic islets begins at about 4-6 weeks of age and by 7 months of age about 80-90% of female NOD mice and 30-40% of male NOD mice develop the disease.

In this experiment, spleen cells were taken from 4 month old male or female NOD mice and the spleen cells ($10^8$) were activated with the T-cell mitogen concanavlin A (Con A; 1.25 µg/ml) by culture in vitro for 48 h. The resulting T-cell blasts were likely to include the autoimmune T-cells because such T-cells are known to transfer IDDM to young, pre-diabetic NOD mice. The T-cells were then treated with 8-MOP-UVA exactly as described in Example 1 except that membranes were not isolated; the whole treated cells were used.

Groups of 10 male NOD mice and 12 female NOD mice were either sham-vaccinated with saline or vaccinated intraperitoneally with $2 \times 10^7$ treated T-cells at 5 weeks of age (the age of the beginning of the disease process). Repeat vaccinations were done monthly $\times 3$ and the blood glucose of the mice was measured at age 7 months to detect those that developed IDDM (blood glucose greater than 200 mg % on a morning sample of blood).

It can be seen that vaccination with the 8-MPO-UVA treated T-cells prevented IDDM in most of the NOD mice.

TABLE 1

8-MOP-UVA treated T-cells vaccinate NOD mice against IDDM

| Mice | Sex | Incidence of IDDM at 7 months of age |
|---|---|---|
| Sham-vaccinated | male | 4/10 |
| | female | 11/12 |
| Vaccinated | male | 0/10 |
| | female | 3/12 |

From the above and from other experiments, it is apparent that photoactivated cross-linking is a highly effective chemical cross-linking treatment that can be used in the preparation of T-cells and T-cell membranes for the treatment of human autoimmune diseases and for vaccines to induce resistance to autoimmune diseases.

Examples of autoimmune diseases that can be treated using membrane proteins of autoimmune cell lines are as follows, although these examples are not limiting:

| Human autoimmune diseases | Antigen used to activate T-lymphocytes |
|---|---|
| Multiple sclerosis | a) Myelin basic protein extract |
| | b) Crude extract of central nervous system |
| Thyroiditis | a) Thyroglobulin |
| | b) Crude extract of thyroid gland |
| Diabetes (Type I) | Extract of islet cells |
| Ankylosing spondylitis (specific types) | a) Certain Klebsiella bacteria |
| | b) Crude extract of joints |
| Rheumatoid arthritis | a) Crude extract of joints |
| | b) 65 KD heat shock protein |
| Myasthenia gravis | Acetylcholine receptor (α-subunit) |
| Anterior uveitis | a) S antigen |
| | b) Crude extract of retina |

Vaccines against autoimmune diseases are prepared by incorporating whole T-cells treated in accordance with the present invention or membrane fractions thereof into a pharmaceutically acceptable carrier or adjuvant. The vaccines are administered at approximately two to six week intervals, preferably monthly, for a period of up to four inoculations in order to provide sufficient protection against development of the autoimmune disease sought to be protected against. Each inoculation will comprise about $10^7$-$10^8$ cells or an equivalent amount of membrane.

Compositions for alleviating the symptoms of autoimmune disease are prepared by incorporating the sedimented activated T-cell or membrane fractions as obtained above into a pharmaceutically acceptable carrier.

Compositions within the scope of the invention include compositions wherein the active ingredient is contained in an effective amount to alleviate the symptoms of the autoimmune disease treated. Determination of the effective amounts can readily be determined empirically by those of ordinary skill of the art. In general, however, the amounts and manner of administration are the same as that described above for the vaccine.

In addition to the cross-linked T-cells or membrane fractions thereof, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent by weight, and preferably from about 25 to 85 percent by weight, of active ingredient, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired or necessary, to obtain tablets or dragee cores.

Suitable excipients are, in particular, fillers such as sugars, for example, lactose, sucrose, mannitol, or sorbitol, cellulose preparations and/or calcium phosphate, such as tricalcium phosphate or calcium hydrogen phosphate, as well as binders such as starch paste using, for example, maize starch, wheat starch, rice starch, potato starch, gelatin, gum tragacanth, methyl cellulose, hydroxypropylcellulose, sodium carboxymethylcellulose, and/or polyvinyl pyrrolidone. If desired, disintegrating agents may be added, such as the above-mentioned starches and derivatives thereof, as well as carboxymethyl starch, cross-linked polyvinylpyrrolidone, agar, or alginic acid or a salt thereof such as sodium alginate. Auxiliaries include flow-regulating agents and lubricants, such as silica, talc, stearic acid or salts thereof such as magnesium or calcium stearate, and/or polyethylene glycol. Dragee cores may be provided with suitable coatings which, if desired, are resistant to gastric juice. For this purpose, concentrated sugar solutions may be used, which may optionally contain gum Arabic, talc, polyvinyl pyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Pharmaceutical preparations which can be administered rectally include suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a suitable base. Suitable base materials include, for example, liquid triglycerides, polyethylene glycols, and paraffin hydrocarbons.

Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils, such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension may contain stabilizers.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology and terminology employed herein is for the purpose of description and not of limitation.

What is claimed is:

1. A preparation for preventing or treating an autoimmune disease, consisting essentially of T-lymphocyte cells specific for the autoimmune disease, which cells have been activated by having been exposed to an antigen specific for the autoimmune disease or a mitogen capable of inducing an immune response by the T-lymphocyte cells, and which cells have been further treated by contacting said cells with a photoactivatable psoralen cross-linking agent which is selective for a receptor on the cell membrane, said cross-linking agent having been present in an amount sufficient to cause cross-linking to occur on the surface of said cells upon photoactivation, followed by photoactivation of the psoralen cross-linking agent; or cell membranes separated from said treated T-lymphocyte cells.

2. A preparation in accordance with claim 1, wherein the cross-linking agent is selected from the group consisting of psoralen, 8-methoxypsoralen, 4, 5',8-trimethylpsoralen, 4',5'-dihydropsoralen, 3-carbethoxypsoralen, 4',5'-dihydro 3-carbethoxypsoralen, 5-methoxypsoralen, 4'-(hydroxymethyl)-4,5',8-trimethylpsoralen, and aminomethyltrioxypsoralen.

3. A preparation in accordance with claim 1, wherein the cross-linking agent is 8-methoxypsoralen.

4. A preparation in accordance with claim 1, wherein said T-lymphocyte cells are specific for an autoimmune disease selected from the group consisting of multiple sclerosis, thyroiditis, diabetes type I, ankylosing spondylitis, rheumatoid arthritis, myasthenia gravis, and anterior uveitis.

5. A preparation in accordance with claim 1, wherein said preparation consists essentially of whole treated T-lymphocyte cells.

6. A preparation in accordance with claim 1, wherein said preparation consists essentially of the cell membranes separated from said treated T-lymphocyte cells.

7. A method for producing cross-linked activated T-lymphocytes, comprising the steps of:
suspending T-lymphocyte cells specific for an autoimmune disease, which cells have been activated by having been exposed to an antigen specific for the autoimmune disease or a mitogen capable of inducing an immune response by the T-lymphocyte cells, in a buffer;
contacting the suspended cells with a photoactivatable psoralen cross-linking agent which is selective for a receptor on the cell membrane of said cells, in an amount sufficient to cause cross-linking to occur on the cell membrane upon photoactivation; and
photoactivating the psoralen cross-linking agent with light of an appropriate wavelength.

8. A method in accordance with claim 7, wherein the photoactivatable psoralen is -b 8-methoxypsoralen and the light of an appropriate wavelength is UVA.

9. A pharmaceutical composition for preventing or treating an autoimmune disease, comprising an effective amount of a preparation in accordance with claim 1 in a pharmaceutically acceptable carrier.

10. A method for preventing or treating a specific autoimmune disease in a patient, comprising administering to said patient an effective quantity of a composition according to claim 9.

11. A method for treating a specific autoimmune disease in a patient afflicted with said autoimmune disease comprising administering to said patient an effective amount of a composition in accordance with claim 9.

12. A method in accordance with claim 11, wherein said T-lymphocyte cells treated with said photoactivatable cross-linking agent are T-lymphocyte cells removed from said patient which have been exposed to a mitogen capable of inducing an immune response by the T-lymphocyte cells.

13. A preparation in accordance with claim 1, wherein said receptor is the 22 kD cell surface receptor which recognizes 8-methoxypsoralen.

14. A preparation in accordance with claim 1, wherein said treatment with psoralen cross-linking agent comprises contacting about $5-10 \times 10^6$/ml of said cells, suspended in tissue culture medium, with about 50 to about 500 μg/ml of said psoralen cross-linking agent and subjecting said cells to light of suitable wavelength to cause cross-linking of said psoralen for a period of from about 5 to about 60 minutes.

15. A method in accordance with claim 7 wherein said suspending step comprises suspending about $5-10 \times 10^6$/ml of said psoralen cross-linking agent and said photoactivating step comprises subjecting said cells to light of suitable wavelength to cause cross-linking of said psoralen for a period of from about 5 to about 60 minutes.

16. A method in accordance with claim 10 wherein said autoimmune disease is selected from the group consisting of multiple sclerosis, thyroiditis, diabetes type I, ankylosing spondylitis, rheumatoid arthritis, myasthenia gravis, and anterior uveitis.

* * * * *